(12) United States Patent
Metzger et al.

(10) Patent No.: US 6,916,340 B2
(45) Date of Patent: Jul. 12, 2005

(54) TIBIAL PROSTHESIS CONVERTIBLE IN VIVO TO A MODULAR PROSTHESIS

(75) Inventors: Robert M. Metzger, Nappanee, IN (US); Stanley E. Asnis, Port Washington, NY (US)

(73) Assignee: Biomet, Inc., Warsaw (IN)

( * ) Notice: Subject to any disclaimer, the term of this patent is extended or adjusted under 35 U.S.C. 154(b) by 0 days.

(21) Appl. No.: 10/328,453

(22) Filed: Dec. 23, 2002

(65) Prior Publication Data

US 2003/0093156 A1 May 15, 2003

Related U.S. Application Data

(63) Continuation of application No. 09/303,945, filed on May 3, 1999, now Pat. No. 6,500,208, which is a continuation of application No. 09/173,940, filed on Oct. 16, 1998, now abandoned.

(51) Int. Cl.⁷ .................................................. A61F 2/38
(52) U.S. Cl. ............................... 623/20.15; 623/20.28; 623/908
(58) Field of Search ..................... 623/20.15, 20.21, 623/20.28, 901, 902, 908; 264/274; 606/88, 90

(56) References Cited

U.S. PATENT DOCUMENTS

| 4,001,896 A | * | 1/1977 | Arkangel ...................... 623/20 |
| 4,205,400 A | | 6/1980 | Shen et al. .................... 3/1.91 |
| 4,459,985 A | | 7/1984 | McKay ......................... 128/303 |
| 4,479,271 A | * | 10/1984 | Bolesky et al. ........... 623/20.17 |
| 4,501,031 A | | 2/1985 | McDaniel et al. ............ 3/1.911 |
| 4,711,639 A | | 12/1987 | Grundei ......................... 623/20 |
| 4,714,474 A | | 12/1987 | Brooks, Jr. et al. ........... 623/10 |
| 4,795,468 A | | 1/1989 | Hodorek et al. .............. 623/18 |
| 4,892,547 A | | 1/1990 | Brown ......................... 623/20 |
| 4,936,853 A | | 6/1990 | Fabian et al. ................. 623/20 |
| 4,938,769 A | | 7/1990 | Shaw ........................... 623/20 |
| 4,959,071 A | | 9/1990 | Brown et al. ................. 623/20 |
| 4,963,152 A | | 10/1990 | Hofmann et al. ............. 623/18 |
| 4,997,445 A | | 3/1991 | Hodorek ....................... 623/16 |
| 5,007,933 A | | 4/1991 | Sidebotham et al. ......... 623/20 |
| 5,061,271 A | | 10/1991 | Van Zile ....................... 623/20 |
| 5,080,675 A | | 1/1992 | Lawes et al. ................. 623/20 |
| 5,108,442 A | | 4/1992 | Smith .......................... 632/20 |
| 5,282,861 A | | 2/1994 | Kaplan ........................ 623/16 |

(Continued)

FOREIGN PATENT DOCUMENTS

FR 2702651 * 9/1994

OTHER PUBLICATIONS

Windsor, Russell E. et al., "Revision of Well–fixed Cemented, Porous Total Knee Arthroplasty," *The Journal of Arthroplasty*, vol. 3, supplement, 1988, pp. S87–S94.

"Anatomic Axial Alignment Instrumentation," Biomet brochure, Form Y–BMT–387/103194/M, © 1994.

"Maxim® the Complete Knee System—Design Rationale," Biomet brochure, Form Y–BMT–440/061595/M © 1995.

"Maxim® the Complete Knee System," Biomet brochure, Form Y–BMT–394R/121595/M © 1995.

(Continued)

*Primary Examiner*—Brian E Pellegrino
(74) *Attorney, Agent, or Firm*—William F. Bahret (57) ABSTRACT

A nonmodular tibial prosthesis having a retainer for a modular bearing on the superior surface of a tibial base, a nonmodular primary bearing directly molded to the base, and a mechanical release member mounted on the tibial base in contact with the nonmodular primary bearing. The release member includes a wedge portion with a superiorly posteriorly inclined face, and is designed to be driven anteriorly upon actuation so as to force the primary bearing off of the tibial base, after which the primary bearing and release member are removed and replaced with a modular bearing.

13 Claims, 8 Drawing Sheets

U.S. PATENT DOCUMENTS

| | | | |
|---|---|---|---|
| 5,330,534 A | 7/1994 | Herrington et al. | 632/20 |
| 5,344,461 A | 9/1994 | Phlipot | 623/20 |
| 5,387,240 A | 2/1995 | Pottenger et al. | 623/20 |
| 5,395,401 A | 3/1995 | Bahler | 623/20 |
| 5,413,608 A | 5/1995 | Keller | 623/20 |
| 5,443,519 A | 8/1995 | Averill et al. | 623/22 |
| 5,470,354 A * | 11/1995 | Hershberger et al. | 606/102 X |
| 5,549,698 A | 8/1996 | Averill et al. | 623/22 |
| 5,571,200 A | 11/1996 | Cohen et al. | 623/22 |
| 5,571,201 A | 11/1996 | Averill et al. | 623/22 |
| 5,609,646 A | 3/1997 | Field et al. | 623/22 |
| 5,639,280 A | 6/1997 | Warner et al. | 623/22 |
| 5,658,342 A | 8/1997 | Draganich et al. | 623/20 |
| 5,683,470 A | 11/1997 | Johnson et al. | 623/20 |
| 5,702,463 A | 12/1997 | Pothier et al. | 623/20 |
| 5,702,464 A | 12/1997 | Lackey et al. | 623/20 |
| 5,782,925 A * | 7/1998 | Collazo et al. | 623/20 |
| 5,824,103 A | 10/1998 | Williams | 623/20 |
| 5,871,545 A | 2/1999 | Goodfellow et al. | 623/20 |
| 5,879,394 A | 3/1999 | Ashby et al. | 623/20 |
| 5,928,286 A * | 7/1999 | Ashby et al. | 623/20 |
| 5,989,472 A * | 11/1999 | Ashby et al. | 264/274 |

OTHER PUBLICATIONS

"The HEDROCEL® Acetabular Cup—Solutions to Deficiencies in Contemporary Acetabular Cup Design and Materials," Implex Corp., Oct. 21, 1997.

"Design Goal: Elimination of the Factors Contributing to THR Failure," Implex Corp. advertisement, *The American Journal of Orthopedics*, Apr. 1998, vol. XXVII, No. 4, p. 245.

NexGen system, Design Rationale, Zimmer, cover and pp. F.22–F.23 1995 Zimmer Inc.

NexGen, Complete Knee Solution, Zimmer, cover and p. 25 1995 Zimmer Inc.

Johnson & Johnson Orthopaedics, P.F.C. Modular Total Knee System with SPECIALIST®, cover and p. 77 J & J Inc. Nov. 1994.

Duracon® The Tibial System, Howmedica, cover and p. 7 © 1993 & 1994 Howmedica.

Duracon® Knee System, Surgical Technique, Howmedic Osteonics, cover and p. 34 1999 Howmedica.

* cited by examiner

TIBIAL PROSTHESIS CONVERTIBLE IN VIVO TO A MODULAR PROSTHESIS

CROSS-REFERENCE TO RELATED APPLICATION

This application is a continuation of application Ser. No. 09/303,945, filed May 3, 1999, now U.S. Pat. No. 6,500,208, issued Dec. 31, 2002, which is a continuation of application Ser. No. 09/173,940, filed Oct. 16, 1998, abandoned.

BACKGROUND OF THE INVENTION

This invention relates to surgically implantable joint prostheses and, more particularly, to a joint prosthesis that combines advantages of modular and nonmodular prostheses.

Artificial joints of the human body, including in particular knee and hip joints, have been available for 50 years or more and have been the subject of intense development for at least the last 20 years. The earliest designs provided metal-to-bone or metal-to-metal contact between the articulating surfaces of a joint. Friction and wear were significantly reduced in subsequent designs by the introduction of ultra-high molecular weight polyethylene (UHMWPE) as a load-bearing surface. For example, a typical knee joint prosthesis has a tibial component with a polyethylene load-bearing surface in contact with a metal femoral component. Early designs of this type had polyethylene cemented to the tibia, but it is conventional today to secure a polyethylene bearing to a metal base or tray which is anchored in the tibia, typically with the aid of a stem or peg extending into the medullary canal of the tibia.

Numerous methods of securing a polyethylene bearing to a metal base have been developed over the years, as exemplified by the following patents:

| Patent No. | Inventor | Issue Date |
| --- | --- | --- |
| 4,205,400 | Shen et al. | Jun. 3, 1980 |
| 4,217,666 | Averill | Aug. 19, 1980 |
| 4,501,031 | McDaniel et al. | Feb. 26, 1985 |
| 4,714,474 | Brooks et al. | Dec. 22, 1987 |
| 4,795,468 | Hodorek et al. | Jan. 3, 1989 |
| 4,822,362 | Walker et al. | Apr. 18, 1989 |
| 4,938,769 | Shaw | Jul. 3, 1990 |
| 4,959,071 | Brown et al. | Sep. 25, 1990 |
| 4,963,152 | Hofmann et al. | Oct. 16, 1990 |
| 4,997,445 | Hodorek | Mar. 5, 1991 |
| 5,061,271 | Van Zile | Oct. 29, 1991 |
| 5,080,675 | Lawes et al. | Jan. 14, 1992 |
| 5,108,442 | Smith | Apr. 28, 1992 |
| 5,330,534 | Herrington et al. | Jul. 19, 1994 |

There are two general types of tibial components: modular and nonmodular. A nonmodular prosthesis has a bearing secured to the base during fabrication in the factory, typically by direct compression molding. A modular prosthesis has a prefabricated bearing designed to be attached to the base during surgery.

A modular prosthesis has several advantages over nonmodular prostheses, one of which is that an assortment of different prostheses, i.e., different base/bearing combinations, can be created in the operating room from a small inventory of separate bases and bearings of various sizes, shapes and other characteristics. With a modular prosthesis, an orthopedic surgeon can implant an appropriate base for the patient and then fit the patient with several trial bearings in the process of selecting an appropriate primary bearing to attach to the implanted base. Modular bearings are often readily removable, and in such cases they have the further advantage of facilitating revision surgery, which may become necessary in cases of traumatic injury or bearing surface wear, by enabling replacement of the bearing without removing the base.

There are also advantages to a nonmodular prosthesis construction, such as design simplicity due to the absence of a need for a retaining mechanism for a removable bearing, and relatively low cost. An even more significant advantage is that a nonmodular tibial component is virtually immune to micromotion at the interface between the bearing and the base.

Micromotion is very difficult to avoid with modular components due to the need for clearances between bearing and base to ensure that they fit together during assembly in the operating room. A very secure locking method may avoid the problem, but nonmodular fabrication of the prosthesis, e.g., direct compression molding of a bearing onto a base, avoids the issue. Unfortunately, a nonmodular prosthesis has heretofore made revision surgery more difficult in that the entire prosthetic component must be removed and replaced. In addition to the extra operating time involved and extraction tools required, such as described in U.S. Pat. No. 4,459,985 to McKay, removal and replacement of the base requires sacrificing the existing fixation to the bone and has associated complications, including possible bone loss or fracture and the difficulty of reestablishing solid fixation. Nevertheless, it is conventional wisdom regarding a nonmodular prosthesis, as stated in the above-referenced Smith patent, that "the bearing component cannot be changed without changing the base component."

SUMMARY OF THE INVENTION

The present invention combines advantages of modular and nonmodular designs with a nonmodular tibial prosthesis that is convertible in vivo to a modular device. The prosthesis includes a tibial base having a retainer for a modular tibial bearing, and has a nonmodular primary bearing secured to the tibial base. According to one aspect of the invention the retainer includes a raised portion with a cavity in an inwardly facing surface thereof, and according to another aspect of the invention the retainer is adapted to cooperate with an auxiliary mechanical locking element to securely retain a modular bearing on the base.

A retainer as that term is used herein is a part of the tibial base that is capable, alone or in conjunction with an auxiliary element or elements, of retaining a modular bearing in place on the base. It may be formed on the base as a one-piece or multi-piece retainer.

According to a further aspect of the invention, a mechanical release member is mounted on the tibial base in contact with the primary bearing as a part of the nonmodular tibial prosthesis designed to be actuated during revision surgery. Upon actuation, the release member forces the primary bearing off of the tibial base, after which the primary bearing and release member are removed and replaced by a modular bearing. In some cases, conversion to a modular device would be a desirable option even during the primary surgery. It is routine for surgeons to check the patient's range of motion before and after selecting the appropriate size of tibial component and cementing the base to the tibial plateau. With a nonmodular prosthesis the surgeon has little recourse but to dislodge the cemented base and remove it and all the cement from the tibia if the final range-of-motion check is unsatisfactory. The present invention provides a desirable alternative.

A general object of the present invention is to provide an improved surgically implantable joint prosthesis.

Another object of the present invention is to provide advantages of a nonmodular joint prosthesis, including the virtual absence of micromotion, and yet allow a surgeon performing revision surgery to change to a modular bearing without disturbing the base member and thereby jeopardizing fixation.

Another object of the invention is to extend the lifetime of an artificial joint.

These and other objects and advantages of the present invention will be more apparent upon reading the following detailed description of the preferred embodiment in conjunction with the accompanying drawings.

DETAILED DESCRIPTION OF THE PREFERRED EMBODIMENT

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Figure 1:
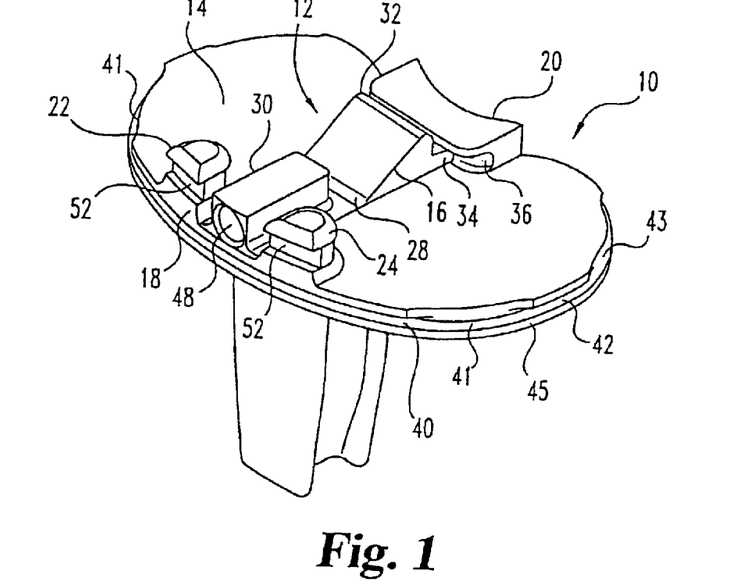
FIG. 1 is a perspective view of a tibial base or tray with a release member slidably mounted thereon according to the preferred embodiment of the present invention.
Figure 1A:
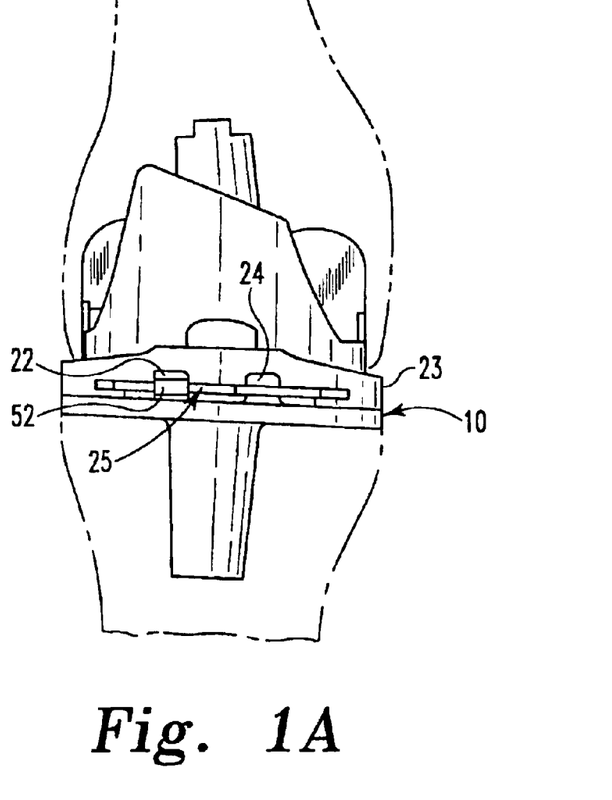
FIG. 1A is an anterior view of a knee joint prosthesis including a modular bearing retained with the aid of a locking clip on the tibial base of FIG. 1 with the release member removed therefrom.
Figure 1B:
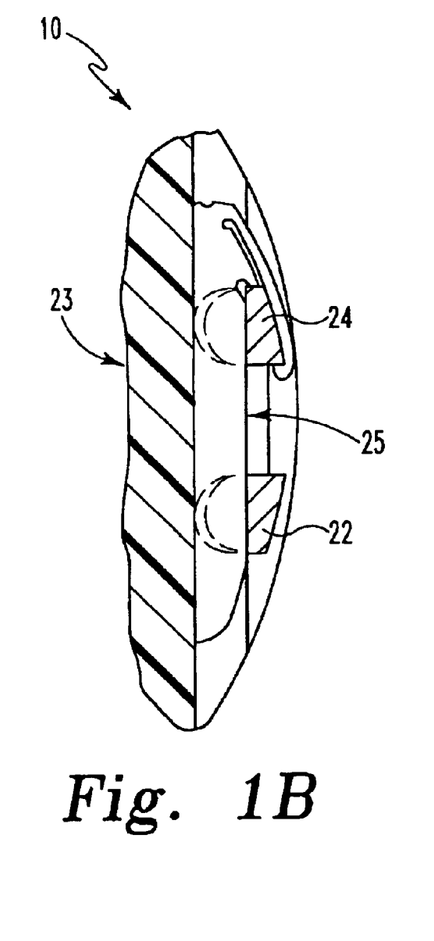
FIG. 1B is a top sectional view of the anterior portion of the tibial component of FIG. 1A further illustrating the locking clip.

With reference to FIG. 1, the preferred embodiment of the present invention includes a tibial base or tray 10 and a release member 12 slidably mounted on the intercondylar portion thereof on a smooth, flat superior surface 14. Release member 12 includes a wedge portion 16 and extends between the anterior edge 18 of base 10 and a retaining rail 20 extending superiorly from the posterior edge of the base. Tibial base 10 includes a pair of posts 22 and 24 integrally formed on the superior surface 14 of the base at the anterior edge thereof. As shown in FIGS. 1A and 1B and as described in further detail in U.S. Pat. No. 5,330,534, which is hereby incorporated by reference, the posts and rail are designed to cooperate to retain a modular bearing 23 on the base, the modular bearing preferably being preformed of ultra-high molecular weight polyethylene (UHMWPE) with anterior and posterior recesses to receive the posts and rail, respectively, and with a uniformly flat inferior surface on its intercondylar and medial/lateral portions for direct contact with the superior surface 14 of the base. The modular bearing is designed to be locked in position with a transverse slide-in locking bar or clip 25 wedged between the posts and the bearing in opposed grooves provided therein for that purpose. Modular tibial trays and bearings as generally described above are commercially available from Biomet Inc., the assignee of the present invention, as components of the Maxim® Total Knee System, which includes various sizes and configurations of bases, bearings and stem extensions, as well as femoral and patellar components, for different patient requirements.

Figure 2:
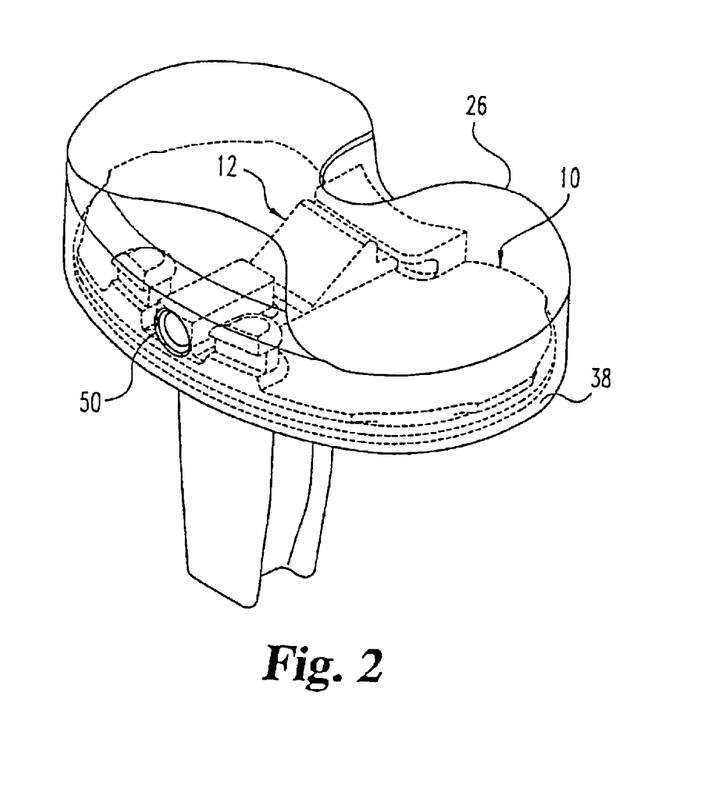
FIG. 2 is a perspective view of a complete nonmodular tibial component according to the preferred embodiment of the present invention.

According to the present invention, a modular bearing is not implanted as the primary tibial bearing but instead is secured to the base during revision surgery after in vivo removal of a primary bearing which has preferably been molded over the base and the release member. Such a primary bearing 26 is shown in FIG. 2 as part of a complete nonmodular tibial component according to the preferred embodiment of this invention. UHMWPE is also a suitable material for the primary bearing, which is preferably molded by direct compression molding in a conventional manner.

Release member 12 is preferably formed as a single piece with the thinner, anterior end 28 of wedge 16 integrally joined to an internally threaded drive block 30 and the thicker, posterior end 32 of the wedge integrally joined to a tail 34 which is sized and shaped to partially plug a transverse groove or channel 36 formed in the inwardly facing surface of rail 20. The wedge suitably has an anterior-posterior length of approximately 0.5", a width of approximately 0.5", and a height of approximately 0.25". The one-piece release member is suitably made of biocompatible titanium machined in a conventional manner, or may be cast cobalt-chromium. Its surfaces are preferably all smooth.

The shape of the release member is shown in greater detail in FIGS. 3–6, from which it can be appreciated that the molded bearing conforms to the shape of the base and release member, filling all exposed spaces within the mold cavity, which is sized with respect to the base to provide a skirt 38 which covers the peripheral edge of the base and fills an elongated anterior edge groove 40, two medial/lateral edge grooves 42 and two posterior edge grooves 44 in the base as shown in the drawings. The skirt thus cooperates with other portions of the molded bearing, as will be described, to secure the bearing to the base. To the extent that any polyethylene wear debris may be produced at the bearing-base interface due to micromotion, the skirt also tends to contain such debris. The thickness of the skirt adjacent to each such groove, measured in the plane of the superior surface 14 of the tibial base, is suitably approximately 0.020–0.030". The skirt thickness in that plane is correspondingly greater at the edge portions 41 and 43 of the base, where the edge of the base is cut away from its superior surface to the superior surface of a ledge 45 which partially defines the grooves. Preferably the inferior edge 46 of the skirt is trimmed after molding such that it is not flush with the interior surface 47 of the base, as will be explained, in order to minimize the chances of contact with bone cement during implantation.

Each peripheral edge groove 44 extends from the posterior end of its respective edge portion 43 to within 0.1" of the adjacent edge of rail 20. The base has no groove in its posterior edge between the medial and lateral edges of rail 20, as perhaps best shown in FIG. 6. The threaded hole 48 in block 30 is a #12–24 hole and is plugged during the molding process by a set screw (not shown) which is later removed and which may, if desired, extend out of the hole virtually to the mold cavity wall to facilitate the creation of an access hole 50 for an extractor, as will be described, in the anterior surface of the bearing. A manual or automatic trimming step is contemplated to clear any residual polyethylene out of the desired hole 50, which is suitably circular but may be square or otherwise shaped. The threaded hole in block 30 may be left unplugged in the tibial component as implanted.

Figure 4:
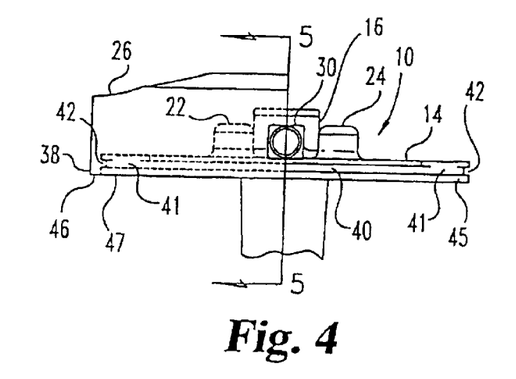
FIG. 4 is an anterior view of the tibial component of FIG. 2 with one side of the bearing cut away to reveal portions of the base and release member and with the majority of the stem removed for illustration purposes.
Figure 5:
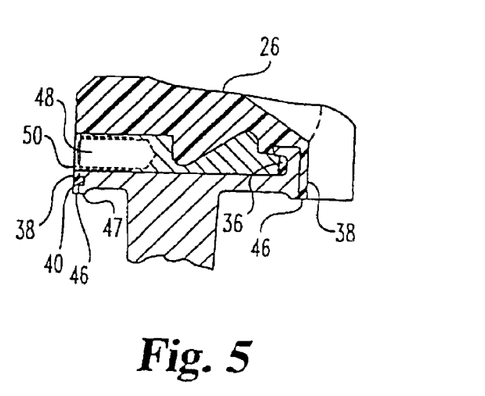
FIG. 5 is a cross-sectional view of the tibial component taken along lines 5—5 in FIG. 4.

Transverse groove 36 in rail 20 is partially plugged by tail 34 and partially exposed in the mold, as perhaps best illustrated in FIGS. 1 and 5, and it is filled with polyethylene during the molding process to the extent so exposed. Anterior grooves 52 and posterior grooves 54 in posts 22 and 24 are entirely exposed and are thus entirely filled with polyethylene in the preferred embodiment during the molding process. Incidental molding of polyethylene also occurs in the space between the release member and the superior surface of the base at the medial and lateral edges of the inferior surface of the release member, which edges are chamfered to match the radius of curvature of posts 22 and 24 as best illustrated in FIG. 4. The chamfered edges preferably extend the entire length of the release member. The inferior surface of the release member is otherwise smooth and flat. The medial and lateral edges of the superior surface of the wedge at its posterior end 32 may also be rounded if desired to maintain a particular bearing thickness at such points.

The portions of the molded primary bearing lying in the grooves in the posts and rail, including the portion of groove 36 directly posterior to tail 34 as well as the portions of groove 36 on either side of the tail, cooperate with each other and with the molded bearing portions in peripheral edge grooves 40, 42 and 44 to secure the primary bearing on the tibial base. An example set of groove dimensions suitable for this purpose is set forth below:

| Groove No. | Height | Width | Depth |
| --- | --- | --- | --- |
| 36 | .125" | .8" | .1" |
| 40 | .06" | 2.2" | .04" |
| 42 | .06" | .4" | .04" |
| 44 | .06" | .5" | .04" |
| 52 | .125" | .3" | .05" |
| 54 | .1" | .25" | .1" |

The dimensions in the above table are most suitable for a tibial base having a nominal size of 71 mm, i.e., a maximum medial/lateral dimension of 71 mm. The peripheral edge groove widths for other base sizes would preferably vary in approximate proportion to base size.

The tibial component with the bearing as shown in FIG. 2 is designed for cases in which the posterior cruciate ligament is retained. Preferably, the same tibial base can accommodate bearings for cruciate-retaining applications and bearings for cruciate-substituting applications, where the tibial component is subjected to higher moments at the implant-bone interface. As is known in the art, the bearing in a cruciate-substituting prosthesis includes a stabilizing post which projects superiorly from the articulating surface level. With the knee loaded in a flexed position, such a stabilizing post experiences an anteriorly directed force due to the absence of the posterior cruciate ligament. The force creates a moment about the transverse axis through the posts on the base that, if not counteracted, would cause the posterior edge of the bearing to lift off of the base. The base and posterior stabilized bearing must cooperate to withstand the load that is normally carried by the posterior cruciate ligament, and the tibial base as described above is so designed.

More specifically, the tibial component with the base and release member as described above has a molded bearing retention force, measured in terms of the maximum anteriorly directed force against a posterior stabilized bearing that the tibial component can sustain without dissociation, in excess of 400 lbs., which is well above the maximum expected in vivo load of 320 lbs. This retention force has been measured in a worse-case scenario in which the base is made in the minimum size presently available in the Maxim® product line (59 mm) and the bearing is molded to the base with the maximum rated polyethylene thickness presently available in the Maxim® product line (24 mm), with no compressive load. The test is performed by connecting a Maxim® femoral component to the tibial component at 90° flexion and then loading the femoral component axially to create an anterior force against the stabilizing post on the tibial bearing. The retention force would be greater with larger base sizes.

Figure 6:
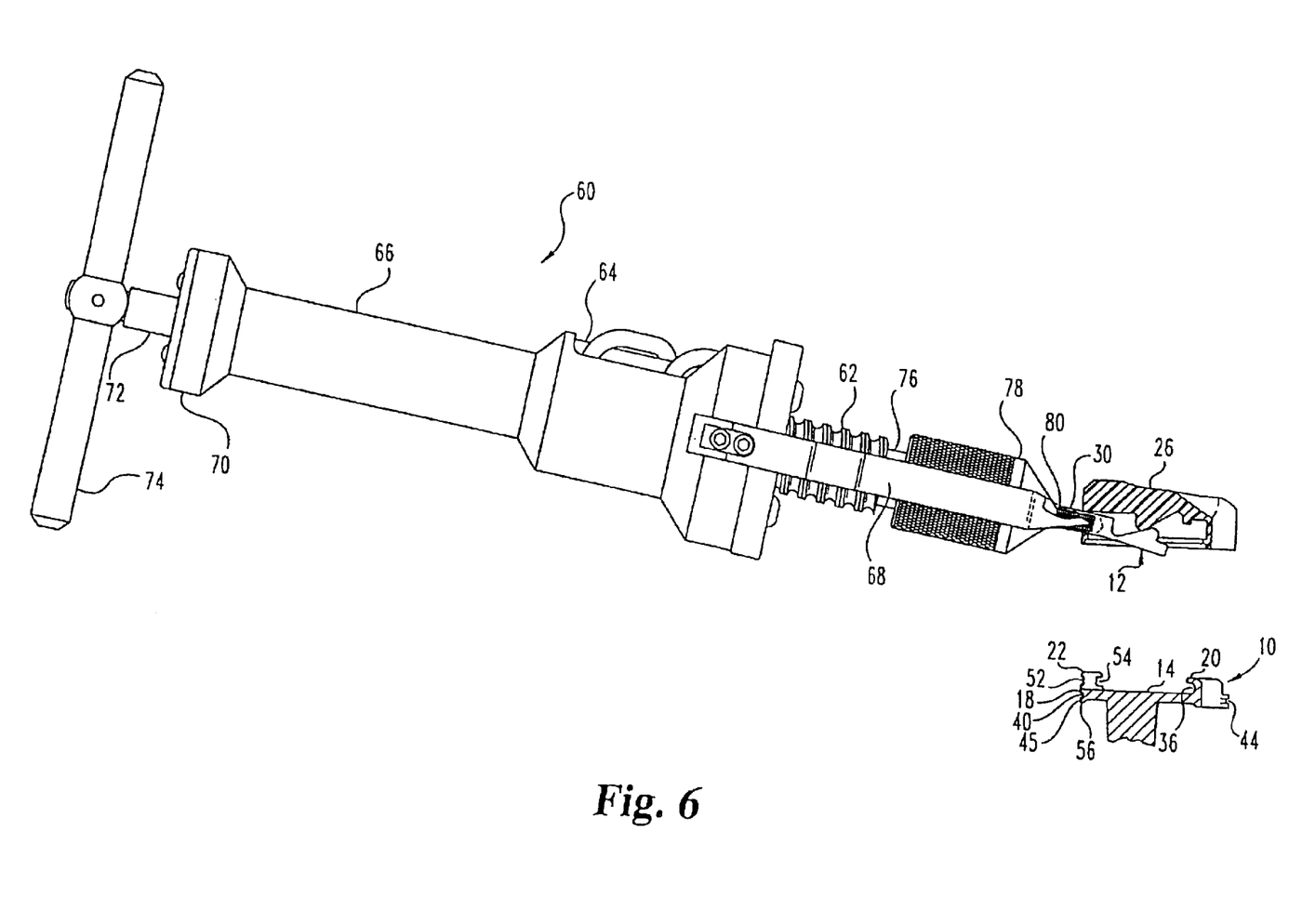
FIG. 6 is a side view of an extractor together with a side cross-sectional view of the tibial component of FIG. 2 illustrating the disengagement of the primary bearing from the base upon actuation of the release member with the aid of the extractor.

Referring now to FIG. 6, the molded primary bearing is removed by actuation of the release member with the aid of an extractor 60 having a ball screw 62 enmeshed with a recirculating ball nut 64 that is nonrotatably mounted in a casing 66 having an axially extending prong 68 mounted on the distal end thereof on either side of the ball screw as a brace for the extractor. Each prong 68 has a pointed tip, one of which is partially cut away in FIG. 6 to reveal a portion of a threaded nose on a conical adapter, as will be described below. A suitable ball screw for such purposes is commercially available from Thomson Saginaw Ball Screw Company, Inc., Saginaw, Mich., as Catalog No. 720426SS. A compatible ball nut is the Thomson Catalog No. 5708278 ball nut. A precision steel ball bushing bearing, Thomson Catalog No. A-81420, is mounted in the proximal end 70 of the casing to rotatably and slidably support an unthreaded proximal portion 72 of the ball screw shaft, and a T-handle 74 is mounted on that end of the ball screw shaft for rotation and consequent axial motion thereof. The tool preferably includes a releasable ratchet mechanism (not shown) to prevent clockwise rotation of the ball screw, thereby allowing the surgeon's grip on the T-handle to be temporarily released for repositioning during retraction of the ball screw. The ball screw shaft also has an unthreaded distal portion 76 on which is rotatably mounted an adapter 78 having an externally threaded nose 80 designed to engage the threaded drive block 30 of release member 12 in the tibial component. Access hole 50 in the bearing is formed with an inner diameter greater than the outer diameter of nose 80 for this purpose.

In operation, the ball screw is advanced sufficiently to position the nose of the adapter axially beyond the prongs, and the nose of the adapter is then inserted through circular hole 50 in the anterior surface of the bearing and threaded into drive block 30 by manual rotation of the adapter. The ball screw is then retracted with the aid of the T-handle, without rotating the adapter. The prongs indent and thus firmly engage the anterior surface of the bearing as the ball screw is retracted, and, with the spacing between the bearing and ball nut fixed by the prongs, the release member is accordingly pulled anteriorly, whereupon the action of the wedge causes the bearing to move superiorly and disengage from the base. The primary bearing is raised to the point of disengagement and then removed with the release member as a unit, as shown in FIG. 6. With the extractor as described above, the maximum translational force required to be exerted to remove a molded primary bearing from a 71 mm tray is approximately 670 pounds, which corresponds to a torque of approximately 30 inch-pounds applied to the handle end of the ball screw shaft. This amount of torque is well within the capability of a surgeon or surgical assistant of normal strength.

Those skilled in the art will appreciate from FIG. 6 and the foregoing description that the translational force exerted by the extractor is applied between the bearing and the release member, thereby avoiding any disturbance to the base. The bearing is removed substantially in one piece, although fragments of polyethylene may remain on the base, such as in posterior grooves 54 of posts 22 and 24. Any such fragments are easily removed, and the primary bearing is then replaced with a modular bearing and locking bar of the type described in the above-referenced U.S. Pat. No. 5,330, 534.

Preferably the skirt on the molded primary bearing is trimmed after molding such that its inferior surface is not flush with the inferior surface 47 of the base, and, if desired, the skirt may be trimmed such that its inferior surface is flush with the superior surface of ledge 45. When the tibial component is implanted, such trimming spaces the bearing apart from the tibial plateau and thus tends to minimize the chances of contact with bone cement, which is often applied to the tibial plateau to help secure the tibial base thereto and which may be present and exposed to some degree adjacent to the periphery of the base. As a result, the primary bearing can be removed by actuation of the release member, as described above, without significant risk of unwanted resistance from bone cement or of any removal or disturbance of bone cement. As an alternative to such trimming, the mold may be modified, if desired, to provide a correspondingly shorter skirt on the bearing.

Figure 3:
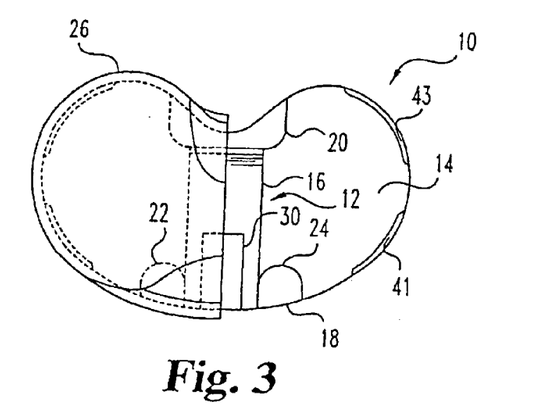
FIG. 3 is a top view of the tibial component of FIG. 2 with one side of the bearing cut away to reveal portions of the base and release member.

The modular bearing has no skirt and is no wider than the tibial base, and is therefore slightly smaller than the primary bearing, which extends slightly beyond the peripheral edge of the base as described above and as shown, e.g., in FIGS. 3 and 4. Alternatively, the modular bearing may be made as wide as the primary bearing it is designed to replace, such that it likewise extends slightly beyond the peripheral edge of the base, albeit without a skirt.

A one-piece construction is preferred for the tibial base. The base may be machined from titanium with an integral stem but is preferably cast of cobalt-chromium. While a stem is a preferred part of the tibial component, the principles of the invention also apply to a stemless tibial base.

Figure 7:
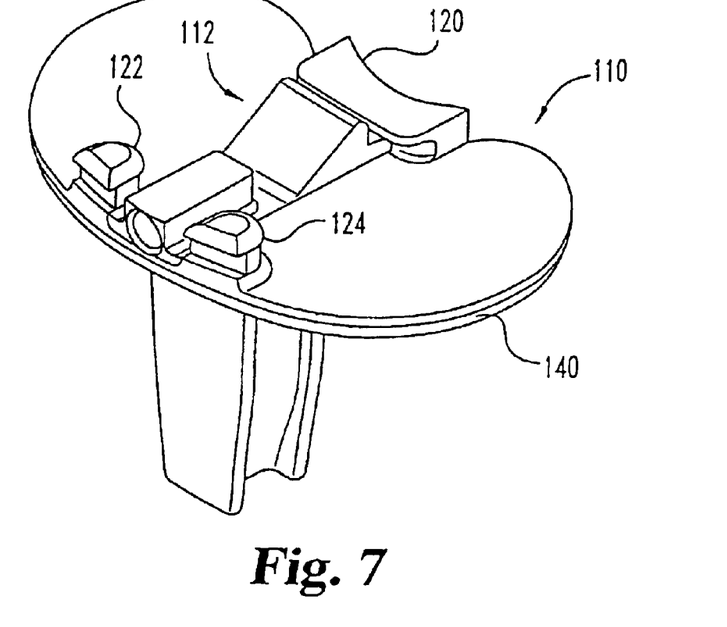
FIG. 7 is a perspective view of a tibial base or tray with a release member slidably mounted thereon according to a first alternative embodiment of the present invention.
Figure 8:
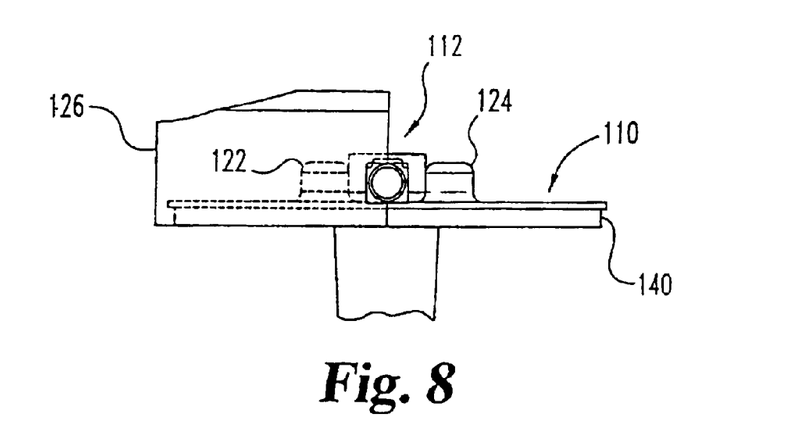
FIG. 8 is an anterior view of the tibial component of FIG. 7 with one side of the primary bearing cut away to reveal portions of the base and release member.

A first alternative embodiment of a nonmodular tibial component according to the present invention is shown in FIGS. 7 and 8. In this embodiment, a base 110 has an undercut portion 140 which is filled with polyethylene during the molding process and which cooperates with other molded bearing portions as in the preferred embodiment described above to secure the primary bearing on the tibial base. The undercut portion may extend around the entire periphery of the base or selected portions thereof. The construction of the tibial component, including release member 112, posterior rail 120, anterior posts 122 and 124, and molded primary bearing 126, is otherwise the same as that of the preferred embodiment described above. This embodiment may be useful in certain applications, such as in uncemented tibial implants where there is no possibility of contact with bone cement.

Figure 9:
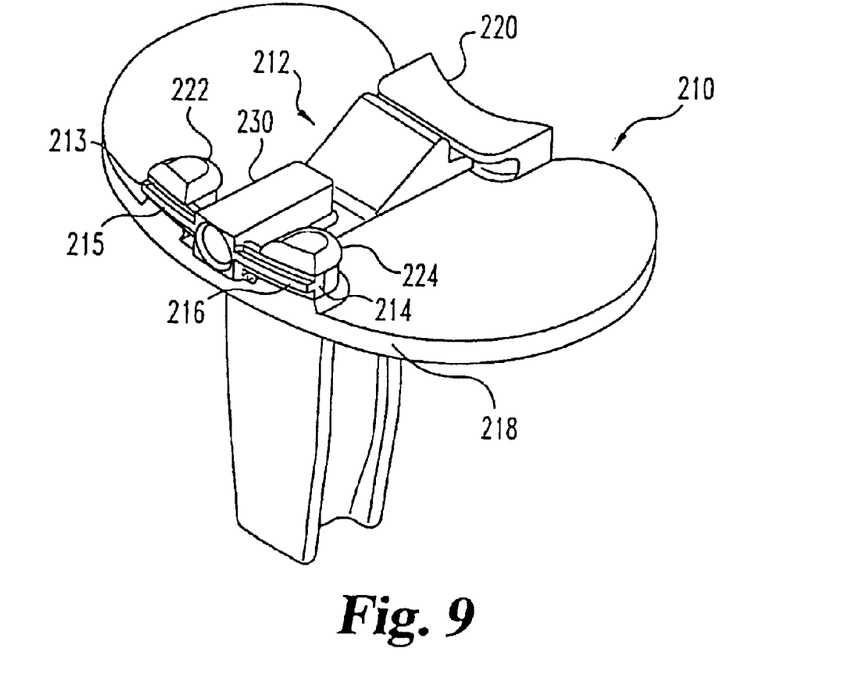
FIG. 9 is a perspective view of a tibial base or tray with a release member slidably mounted thereon according to a second alternative embodiment of the present invention.
Figure 10:
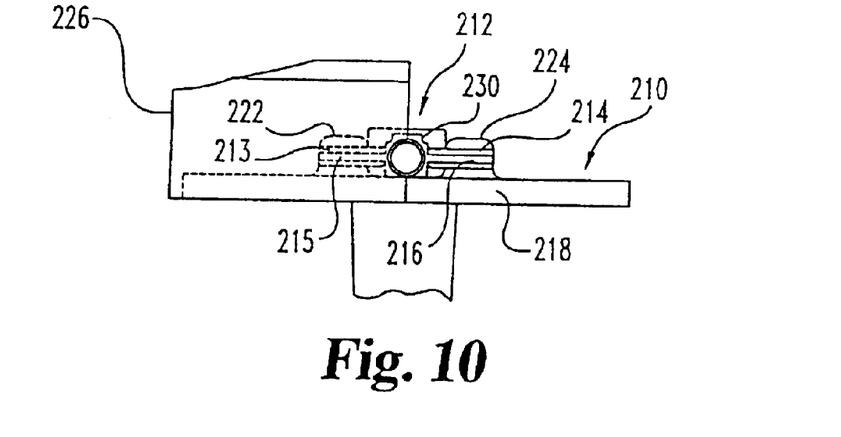
FIG. 10 is an anterior view of the tibial component of FIG. 9 with one side of the primary bearing cut away to reveal portions of the base and release member.

FIG. 9 is a perspective view of a second alternative embodiment of a nonmodular tibial component according to the present invention. In this embodiment the release member 212 is provided with a pair of transverse arms 213 and 214 on the anterior end of the drive block 230. The posterior sides of the transverse arms fill the anterior grooves in posts 222 and 224 provided at the anterior edge of the base 210, and the anterior sides of the transverse arms are provided with respective cutting ridges 215 and 216 each of which extends the length of its arm, as shown in FIG. 9. The cutting ridges are provided to facilitate passage of the anterior end of the release member through the anterior portion of the primary bearing 226 and thereby facilitate forward motion of the release member. A scalpel may be used during revision surgery to cut into or through the relatively thin layer of polyethylene (approximately 0.010–0.020") covering the cutting ridge, if desired, to further facilitate the release action.

In this embodiment, tibial base 210 has a smooth, flat peripheral edge 218 rather than a grooved or undercut edge as in the previous embodiments. Base 210 and the rail 220 and posts 222 and 224 integrally formed thereon are otherwise the same as their counterparts in the preferred embodiment, as is release member 212. Due to the smooth, flat edge and the transverse arms, this embodiment provides less retention force than the previous embodiments, which may be suitable in some circumstances such as in cruciate-retaining applications. The retention force could be increased in this or either prior embodiment by forming the release member without a tail that extends into the channel in the rail. However, in this embodiment the anterior portion of the bearing already tends to disengage from the base well before the posterior portion. It is believed more desirable in most applications to have the anterior and posterior portions of the primary bearing disengage from the tibial base at approximately the same time, i.e., with negligible tilting, as in the preferred embodiment.

The present invention also encompasses other forms of retainers and other methods of removing a molded primary bearing without removing the base. Other retainer forms presently contemplated as useful to varying degrees in certain applications include pegs, posts, holes or other recesses, dovetail configurations, tongue and groove configurations, mortise and tenon configurations, retaining walls, rails, detents, and snap ring grooves.

Figure 11:
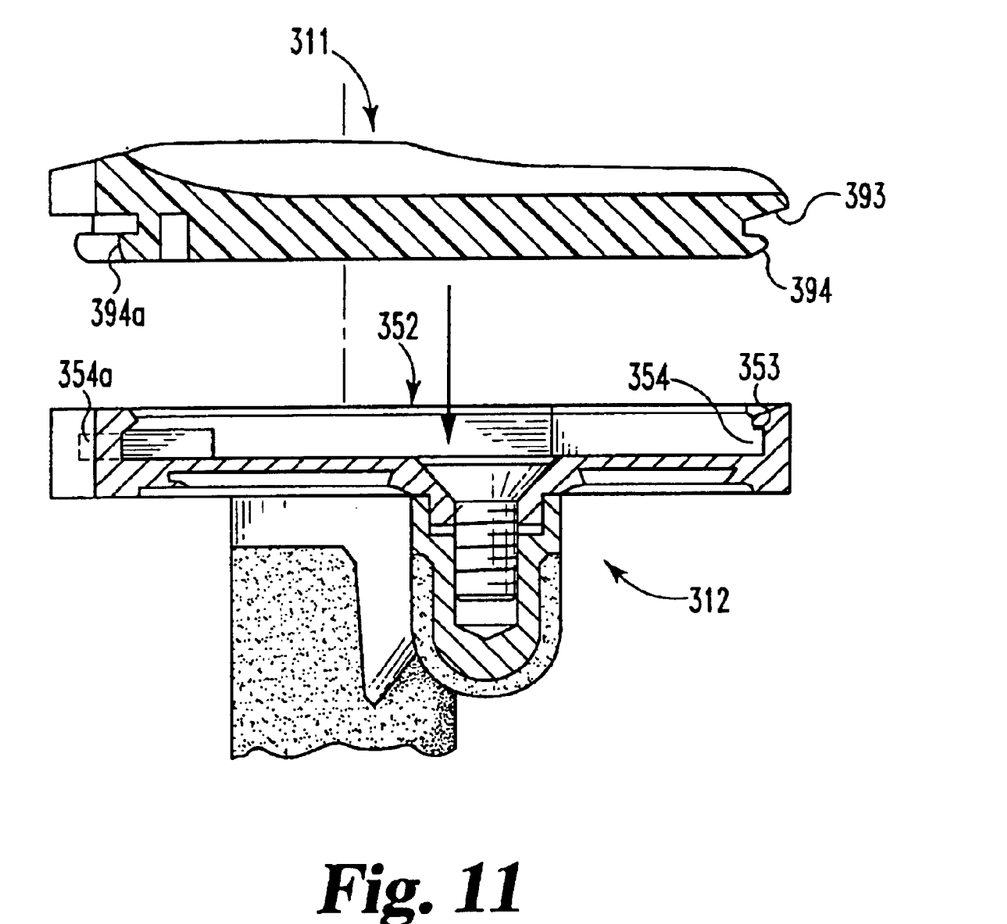
FIG. 11 is a cross-sectional view of one embodiment of a tibial base and modular bearing adapted for snap-fit interconnection.

For example, while the intercondylar posts and rail of the preferred embodiment constitute the preferred form of modular bearing retainer according to the present invention, the retainer may alternatively be in the form of a raised flange or rim about other portions or all of the periphery of the tibial base, with a cavity in an inwardly facing surface of the flange or rim, wherein the modular bearing has a corresponding tongue or lip on its outer edge surface that fits into the cavity, as in U.S. Pat. No. 4,938,769 to Shaw or U.S. Pat. No. 4,795,468 to Hodorek et al. Referring to FIG. 11, tibial tray 312 has a raised flange 352 about its periphery and the flange is contoured at 353 to mate with corresponding contour 393 in bearing insert 311 and is provided with undercuts 354 and 354a to accept tongues 394 and 394a, respectively, of the bearing insert. Bearing insert 311 is then received and retained by these snap-fit means. Alternatively, or in addition as disclosed in the latter patent, the modular bearing may be secured to the base with the aid of an auxiliary locking element in the form of a spring clip that interlocks a groove in the rim wall and a corresponding groove in the outer edge surface of the bearing. The clip is mounted in one groove so as to protrude therefrom and snap into the other groove when the modular bearing is pressed against the base. According to the present invention, the spring clip is preferably not incorporated in the primary tibial prosthesis, and the molded primary bearing preferably extends into the groove in the rim.

Figure 12:
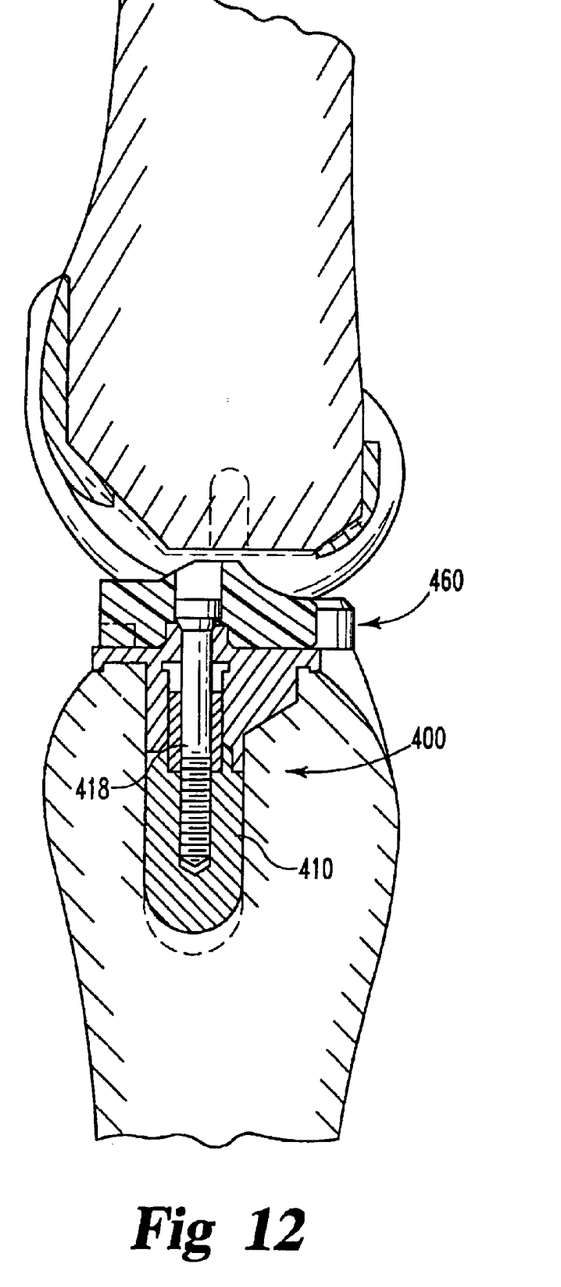
FIG. 12 is a sectional view of one embodiment of a knee joint prosthesis in which a prefabricated bearing is retained on a tibial base with the aid of a threaded fastener.

As another alternative, the base may be provided with a threaded hole or holes designed to cooperate with a screw or screws to securely retain a modular bearing in place after the molded primary bearing has been removed during revision surgery. Such screws thereby serve as auxiliary mechanical locking elements. For example, with reference to FIG. 12, a base 400 with an internally threaded stem 410 designed to retain a modular bearing 460 with the aid of a screw 418, as disclosed in further detail in U.S. Pat. No. 4,959,071 to Brown et al., may be modified to have an undercut peripheral edge and then placed in a mold adapted to provide a polyethylene skirt which covers the peripheral edge and extends into the undercut portion sufficiently to secure the bearing to the base. The threaded stem hole is first plugged with a set screw or otherwise sealed to prevent entry of polyethylene, such as by covering the hole with a stopper of titanium or other suitable material to withstand the heat and pressure in the mold without deformation or fusing to the base.

The molded primary bearing in the alternative embodiment just described is preferably removed in vivo by selectively cutting the skirt at the peripheral edge and then lifting the main portion of the bearing off of the base, using an osteotome if necessary or desired in conjunction with either a preformed slot or a slot that is cut or melted into the polyethylene at that time at the bearing-base interface to facilitate removal. A witness mark may be provided on the bearing edge surface at the time of molding to mark the level of the interface for such purposes. The set screw or stopper in the stem hole is removed after the primary bearing, and a modular bearing is then placed on the base and secured with a screw as described in the above-referenced Brown patent, which is hereby incorporated by reference along with the above-referenced patents to Shaw and Hodorek et al. The removal technique just described may be facilitated by the use of a C-clamp with an osteotome mounted on one end or jaw, with the C-clamp connected across the bearing, e.g., in contact with the medial and lateral edges of the bearing, with the tip of the osteotome inserted into a slot provided for that purpose or aligned with a witness mark. The opposing forces exerted by the C-clamp do not disturb the tibial base. This technique may also be used in lieu of a release member for removal of a bearing molded to any of the tibial bases of FIGS. 1, 7 or 9.

Similarly, a pin may be placed through a coaxial pair of through holes in a modular bearing and base and held in position by a clip as described in U.S. Pat. No. 5,061,271 to Van Zile, which patent is hereby incorporated by reference. The tibial base may have one or more dovetail surface members such as disclosed in the above-referenced Van Zile or Shaw patents.

The retainer may alternatively be designed to allow a modular bearing to float to some degree, either by translation or rotation. For example, a modular bearing may be rotatably mounted on a tibial base and retained thereon by means of an unthreaded hole in the surface of the base in cooperation with a mating stem on the inferior surface of the bearing. Peripheral edge grooves may be provided on the base and filled with polyethylene, as described above with reference to FIG. 1, in order to secure a nonmodular bearing to the base. Similar transversely oriented grooves may be provided at a desired depth within the hole in the base if desired. The nonmodular tibial prosthesis preferably includes a centrally mounted release member having a wedge and drive block similar to that shown in FIG. 1, with the wedge portion wider than the hole in the base.

Also, other forms of release members are contemplated, including one-piece and multi-piece mechanisms. For example, two wedges with complementary inclined surfaces could be provided with a counterdrive mechanism to force the wedges toward or away from each other, depending on their orientation, so as to jointly raise the bearing off of the superior surface of the base.

In another alternative embodiment, the molded primary bearing is adapted to be pulled directly away from the superior surface of the base with the aid of a release member in the form of a simple plate, e.g., a relatively thin disc, located between the bearing and base. A modified form of the extractor shown in FIG. 6 is adapted to engage the plate through an access hole provided in the superior surface of the bearing as molded. The plate has a threaded hole with its axis perpendicular to the superior surface of the base, and is mounted in the intercondylar area of the base in place of the release member shown in FIG. 1. A #12–24 hole is suitable as in the preferred embodiment. A through hole coaxial with the hole in the plate is provided in the superior surface of the bearing as an access hole for a threaded nose of an extractor as shown in FIG. 6 but modified to have a longer nose for this purpose. The extractor is adapted to be aligned with the access hole axis with a fixed spacing between the extractor casing and the tibial base. This spacing may be maintained with prongs as shown in FIG. 6 but spaced further apart so as to straddle the bearing and engage contact points provided on the base for this purpose. The contact points may, for example, be peripheral extensions of ledge 45 on the base of FIG. 1 which are not covered with polyethylene during the molding process. If the prongs have pointed tips as in the embodiment of FIG. 6, each contact point on the base preferably has an indentation in its superior surface to receive a prong tip and fix its position in the transverse plane. The base is otherwise the same as shown in FIG. 1.

In operation, the extractor is positioned with the prongs on the contact points on the base and the extended nose of the extractor threaded into the plate. The ball screw of the extractor is then retracted, whereby the plate exerts a superiorly directed force against the bearing and thus raises it off of the base surface. For this purpose, the shear area of the portion of the molded bearing above the plate is greater than the total shear area of the portions of the molded bearing in the grooves in the posts, rail and peripheral edges of the base.

As an alternative to prongs of the type shown in FIG. 6, the extractor may be provided with a pair of jaws with opposed sharp edges adapted to cut into the peripheral skirt on the bearing and engage the medial/lateral edge grooves 42 in the tibial base, whereby the extractor may be clamped to the base. With the nose of the extracter threaded into the plate, the primary bearing may be pulled directly away from the superior surface of the base along with the release plate upon retraction of the ball screw in the extractor.

Alternatively, the primary bearing may be removed in vivo by sectioning, reaming or grinding the bearing or key points thereof. For example, a bearing of the type shown in FIG. 2 but molded to the base 10 without a release member thereon may alternatively be removed by sectioning. More specifically, a medial-lateral strip ¼" to ½" wide may be cut out of the bearing with a saw or mill, and the remaining anterior and posterior bearing portions may then be forced toward each other, and thereby disengaged from the posts, the rail and the edge grooves on the base, with the aid of pliers or a clamp adapted with prongs or otherwise to pierce or otherwise firmly engage the anterior and posterior bearing surfaces.

Reamers, saws and osteotomes may disturb a prosthesis or damage it, e.g., by scratching the smooth superior surface of a tibial base. Therefore, while methods involving such tools are options for revision procedures, it is preferred to incorporate a release member in the nonmodular prosthesis which allows a bearing to be removed without the application of force to the base member.

It is also contemplated that the nonmodular bearing may be secured in ways other than by molding in certain applications. For example, an interference fit may be provided between a preformed bearing and a mating base with the aid of a press in the factory. Thermally aided assembly is another alternative. For example, a barbed central post on the base may be heated so as to locally melt the polyethylene in a preformed bearing as the bearing is pressed onto it; upon cooling, the polyethylene is secured to the post and thereby to the base, which may be provided with ancillary retaining elements such as a retaining rim. A nonmodular prosthesis may also be fabricated using a permanent adhesive to secure a preformed bearing to a base. Such methods are considered possible although not preferred. A recess must be provided in the bearing's inferior surface for a release member if one is desired for the intended application.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed:

1. A method of replacing a knee joint, comprising:
   providing a tibial base with a retainer for a prefabricated replacement bearing to be secured to said tibial base after removal of a primary bearing therefrom;
   direct compression molding a primary bearing to said tibial base;
   implanting said tibial base with said retainer and primary bearing in a patient during primary knee replacement surgery;
   removing said primary bearing during revision surgery without removing said tibial base; and
   securing a prefabricated replacement bearing to said retainer during said revision surgery.

2. A method of revising a tibial prosthesis having a tibial base with a primary bearing directly molded thereto in a mold, comprising:
   during revision surgery, and with said tibial base affixed to a patient's tibia, removing a primary bearing secured to said tibial base by direct molding in a mold; and
   securing a prefabricated replacement bearing to said tibial base during said revision surgery after removal of said directly molded primary bearing without sacrificing the existing fixation to the patient's tibia.

3. A method of revising a tibial prosthesis having a tibial base with a primary bearing direct compression molded thereto, comprising:
   removing said direct compression molded primary bearing during revision surgery without removing said tibial base; and
   securing a prefabricated replacement bearing to said tibial base during said revision surgery.

4. A method of revising a tibial prosthesis having a tibial base with a primary bearing directly molded thereto in a mold, comprising:
   during revision surgery, applying a distraction force to said primary bearing and said tibial base with a release member which is interposed between said tibial base and said primary bearing during fabrication of the prosthesis;
   removing said directly molded primary bearing without removing said tibial base; and
   securing a prefabricated replacement bearing to said tibial base during said revision surgery.

5. The method of claim 4, wherein said removing of said primary bearing is performed with the aid of an extraction tool including a brace and means for engaging said release member.

6. A method of revising a tibial prosthesis having a primary bearing secured to a tibial base such that the primary bearing is unremovable in vivo without damage to the bearing in the process of removal, comprising:
   removing said primary bearing during revision surgery without removing said tibial base; and
   during said revision surgery, mechanically securing a prefabricated replacement bearing to said tibial base in a different manner than that used for securing said primary bearing.

7. The method of claim 6, wherein said prefabricated replacement bearing is secured to said tibial base with the aid of an auxiliary mechanical element of a type not used to secure said primary bearing to said tibial base.

8. The method of claim 6, wherein said removing of said primary bearing is performed with the aid of a release member which is interposed between said tibial base and said primary bearing during fabrication of the prosthesis.

9. The method of claim 8, wherein said removing of said primary bearing is performed with the aid of an extraction tool including a brace and means for engaging said release member.

10. A method of revising a tibial prosthesis having a primary bearing secured to a tibial base such that the primary bearing is unremovable in vivo without damage to the bearing in the process of removal, comprising:

removing said primary bearing during revision surgery without removing said tibial base; and during said revision surgery, mechanically securing a prefabricated replacement bearing to said tibial base in a different manner than that used for securing said primary bearing, wherein said primary bearing is direct compression molded to said tibial base.

11. A method of revising a tibial prosthesis having a primary bearing secured to a tibial base during factory fabrication of the prosthesis, comprising:

removing said factory-secured primary bearing during revision surgery without removing said tibial base wherein said primary bearing is direct compression molded to said tibial base; and securing a prefabricated replacement bearing to said tibial base during said revision surgery.

12. The method of claim 11, wherein said removing of said primary bearing is performed with the aid of a release member which is interposed between said tibial base and said primary bearing during fabrication of the prosthesis.

13. The method of claim 12, wherein said removing of said primary bearing is performed with the aid of an extraction tool including a brace and means for engaging said release member.

* * * * *

UNITED STATES PATENT AND TRADEMARK OFFICE
CERTIFICATE OF CORRECTION

| | | |
|---|---|---|
| PATENT NO. | : 6,916,340 B2 | |
| APPLICATION NO. | : 10/328453 | |
| DATED | : July 12, 2005 | |
| INVENTOR(S) | : Robert G. Metzger et al. | |

It is certified that error appears in the above-identified patent and that said Letters Patent is hereby corrected as shown below:

On the Title Page, item [75] Inventors, change "Robert M. Metzger" to -- Robert G. Metzger--.

Signed and Sealed this

First Day of May, 2007

JON W. DUDAS
*Director of the United States Patent and Trademark Office*